United States Patent
Madsen

(10) Patent No.: US 6,383,160 B1
(45) Date of Patent: May 7, 2002

(54) VARIABLE ANTI-SIPHON VALVE APPARATUS AND METHOD

(75) Inventor: Joseph R. Madsen, Newton, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 09/301,997

(22) Filed: Apr. 29, 1999

(51) Int. Cl.⁷ .............................................. A61M 5/00
(52) U.S. Cl. .................................... 604/10; 604/167.03
(58) Field of Search ........................ 604/8–10, 65–67, 604/167.03, 247, 264

(56) References Cited

U.S. PATENT DOCUMENTS

| | | | |
|---|---|---|---|
| 3,886,948 A | | 6/1975 | Hakim |
| 3,889,687 A | | 6/1975 | Harris et al. |
| 3,985,140 A | * | 10/1976 | Harris |
| 3,991,768 A | | 11/1976 | Portnoy |
| 3,999,553 A | | 12/1976 | Spitz et al. |
| 4,332,255 A | | 6/1982 | Hakim et al. |
| 4,387,715 A | | 6/1983 | Hakim et al. |
| 4,551,128 A | | 11/1985 | Hakim et al. |
| 4,595,390 A | | 6/1986 | Hakim et al. |
| 4,610,658 A | * | 9/1986 | Buchwald |
| 4,621,654 A | | 11/1986 | Holter |
| 4,673,384 A | | 6/1987 | Marion |
| 4,676,772 A | * | 6/1987 | Hooven |
| 4,681,559 A | * | 7/1987 | Hooven |
| 4,729,762 A | | 3/1988 | Doumenis |
| 4,787,886 A | * | 11/1988 | Cosman |
| 4,795,437 A | | 1/1989 | Schulte et al. |
| 4,867,741 A | | 9/1989 | Portnoy |
| 5,192,265 A | | 3/1993 | Drake et al. |
| 5,336,166 A | * | 8/1994 | Sierra |
| 5,634,894 A | | 6/1997 | Magram |
| 6,050,969 A | * | 4/2000 | Kraus |
| 6,090,062 A | | 7/2000 | Sood et al. ..................... 604/9 |

OTHER PUBLICATIONS

Nolte, J., "Ventricles and Cerebrospinal Fluid." In *The Human Brain: An Introduction to its Functional Anatomy*, Mosby Year Book eds., pp. 48–897 (1993).

* cited by examiner

*Primary Examiner*—Angela D. Sykes
*Assistant Examiner*—Jeremy Thissell
(74) *Attorney, Agent, or Firm*—Thomas J. Engellenner; Tram Anh T. Nguyen; Nutter McClennen & Fish LLP

(57) ABSTRACT

Variable anti-siphon devices are disclosed for use in cerebrospinal fluid shunt systems. Such devices can include a housing with an internal chamber, an adjustable barrier separating the chamber into two cavities, and a diaphragm that seats itself against the adjustable barrier with a seating force that is proportional to the pressure differential across it. The adjustable barrier advantageously allows the level of anti-siphon protection to be modified. In one embodiment, the height of the adjustable barrier may be varied. In another embodiment, the barrier is moved longitudinally within the internal chamber to vary the volume of each chamber.

36 Claims, 8 Drawing Sheets

VARIABLE ANTI-SIPHON VALVE APPARATUS AND METHOD

BACKGROUND OF THE INVENTION

The present invention relates generally to cerebrospinal fluid (CSF) shunts, and more specifically, to valves that variably moderate the siphoning effect of a hydrocephalus fluid shunt when the patient changes between recumbent and upright positions.

Hydrocephalus is a condition in which cerebrospinal fluid (CSF) accumulates in the ventricles of the brain. This accumulation of fluid increases the pressure within the ventricles and without medical intervention can cause brain damage and/or death to the patient. A common treatment for hydrocephalus is to use a fluid shunt system to drain excess CSF from the cerebral ventricles to a second body cavity, typically the peritoneal cavity. Shunt systems typically include a hollow catheter tube to remove CSF from the cerebral ventricles, a valve to regulate the CSF flow, and a discharge tube to conduct the CSF into the second body cavity. Such shunt systems are typically implanted entirely beneath the patient's skin and remain in place for several weeks or more.

CSF shunt systems are generally effective when the patient is in a recumbent position. However, when the patient stands upright, the shunt system can act as a siphon resulting in over-drainage of CSF from the cerebral ventricles. The pathological consequences of over-drainage of CSF can include engorgement of the veins, cerebral edema, "slit ventricles" and microcephaly.

To inhibit over-draining due to siphoning, some known CSF shunts have incorporated anti-siphoning devices (ASD) as part of their valve mechanisms. These ASD devices attempt to moderate the flow of the CSF when the patient's attitude changes. The two most common types of mechanisms used in conventional anti-siphoning valves are weighted ball check valves and diaphragm valves.

Weighted ball check valves use one or more spherical balls that are more dense than CSF and are disposed within a cavity in the valve housing. The check valve is generally implanted such that the housing is oriented horizontally when the patient is in a recumbent position. The check valve includes a valve seat at the CSF inlet end (the distal end of the drainage catheter) for engaging the spherical ball. When the patient is recumbent, the spherical ball tends to move away from the valve seat, thereby permitting CSF to flow through the valve. As the patient changes orientation by sitting upright or standing, the valve is then oriented vertically with the valve seat at the bottom of the valve. The spherical ball, being denser than the CSF, sinks toward the valve seat and, when seated, stops the flow of the CSF.

Diaphragm-type anti-siphon valves include an elastic diaphragm to regulate CSF flow. The diaphragm is designed to bear against a seat with a force that is a function of the fluid pressure flowing from the cerebral ventricles, the pressure in the drainage tube, and a reference pressure (usually atmospheric pressure) on the opposite surface of the diaphragm. Under normal operation there is little resistance to the flow of the CSF. However, if the patient's attitude is changed by sitting or standing up, the pressure in the discharge tube will fall as the column of fluid drains. This will increase the pressure differential across the diaphragm, thereby causing the diaphragm to seat more firmly against its seat, stopping the flow of CSF.

A major drawback to both of these approaches is that they are static in nature. If the symptoms persist after these devices are implanted into patients there is typically no alternative but to surgically replace the device.

There exists a need for better mechanisms to regulate CSF pressure, particularly in ambulatory patients. A variable anti-siphon valve that can be adjusted to meet the needs of an individual patient without surgery would be desirable.

SUMMARY OF THE INVENTION

Variable anti-siphon devices are disclosed for use in cerebrospinal fluid shunt systems. Such devices can include a housing with an internal chamber, an adjustable barrier separating the chamber into two cavities, and a diaphragm that seats itself against the adjustable barrier with a seating force that is proportional to the pressure differential across it. The adjustable barrier advantageously allows the level of anti-siphon protection to be modified. In one embodiment, the height of the adjustable barrier may be varied. In another embodiment, the barrier is moved longitudinally within the internal chamber to vary the volume of each chamber.

The present invention farther discloses an apparatus that allows the barrier to be adjusted externally to the patient, i.e., without the need for a surgical incision to access the valve. The barrier may be adjusted by the application of an external magnetic field that is magnetically coupled to a mechanism disposed within the housing. In another embodiment the external adjustment is accomplished by a miniature electric motor disposed within the housing and energized by signals generated external to the body.

In a further embodiment, an anti-siphon device valve includes two parallel paths for fluid drainage. One of the paths includes adjustable anti-siphon protection to prevent fluid flow during and after the attitude of the patient changes. The second path has a high fluid flow resistance but no anti-siphon protection. The second path will allow the flow of fluid to relieve excessive pressure to avoid the danger of having an increase in intra-cranial pressure remaining untreated when the patient is standing.

BRIEF DESCRIPTION OF THE DRAWINGS

These and other features and advantages of the present invention will be better understood by reading the following detailed description taken together with the following drawings wherein.

DETAILED DESCRIPTION OF THE INVENTION

Figure 1:
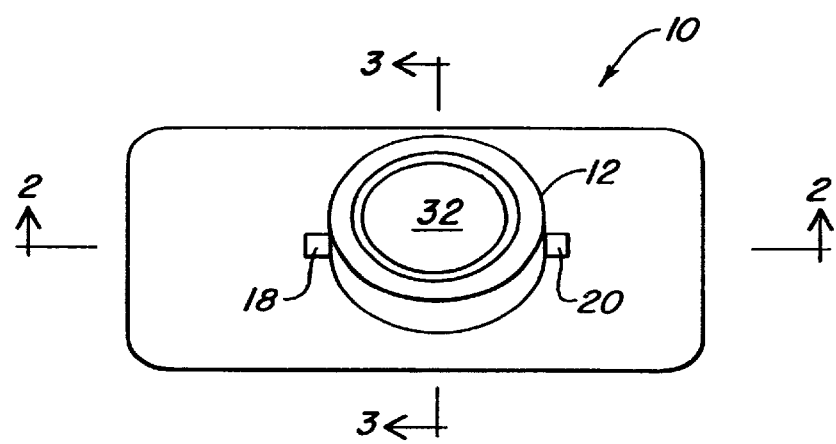
FIG. 1 is a perspective view of a shunt valve having an adjustable anti-siphon mechanism in accordance with the present invention.
Figure 2:
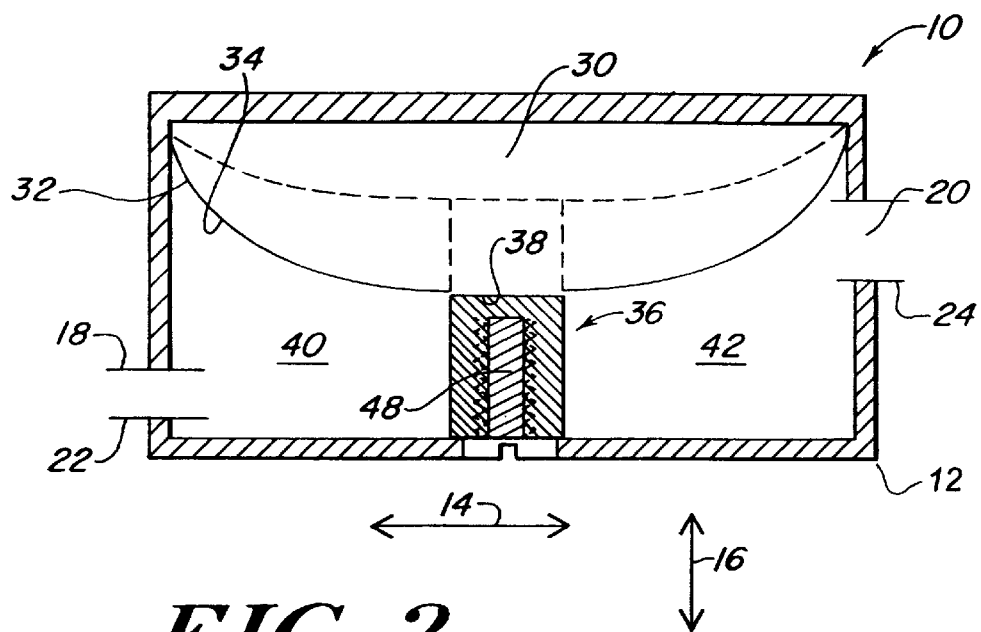
FIG. 2 is a cross-sectional view of the shunt valve of FIG. 1 along line 2—2.

FIGS. 1, 2, 3A and 3B illustrate one embodiment of a shunt valve 10 that provides an adjustable level of anti-siphon protection in accordance with the present invention. The shunt valve 10 includes a housing 12 having a longitudinal axis 14 and a vertical axis 16, an inlet port 18 and an outlet port 20. The housing 12 has an internal chamber 30 in fluid communication with the inlet port 18 and the outlet port 20. The internal chamber 30 has a diaphragm 32 extending across it such that an internal surface 34 of the diaphragm forms a portion of the chamber 30. An adjustable barrier 36 is disposed across the internal chamber 30 so as to separate the chamber into first and second cavities 40,42. The first cavity 40 is in fluid communication with the inlet port 18 and the second cavity 42 is in fluid communication with the outlet port 20. The barrier 36 has a seating surface 38 against which the internal surface 34 of the diaphragm can be seated so as to form a seal. The position of the barrier 36 can be varied to achieve a desired level of anti-siphon protection by selecting a threshold pressure that is effective to dislodge the diaphragm 32 from the barrier thereby allowing fluid to flow through the catheter.

The inlet port 18 is adapted to receive a catheter inlet tubing 22 for connection to a drainage catheter (not shown) inserted into a first region of the spine or brain (not shown) from which CSF is to be removed. The inlet tubing 22 can be constructed separately and attached to the housing 12, or it can be made integral with the housing 12. The outlet port 20 is adapted to receive a catheter outlet tubing 24 to connect to a discharge catheter (not shown) for discharging the cerebrospinal fluid into a second region of the body suitable for receiving the cerebrospinal fluid within the patient, such as the peritoneal cavity. The outlet tubing 24 also may be constructed separately and attached to the housing 12, or it can be made integral with the housing 12.

Figure 3A:
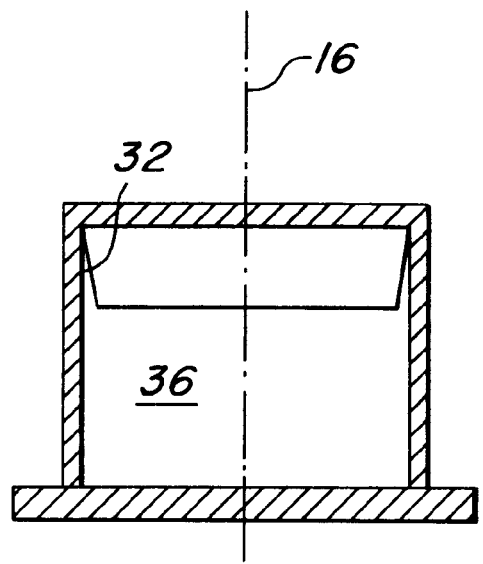
FIG. 3A is a cross-sectional view of the shunt valve of FIG. 1 along line 3—3 showing the anti-siphon mechanism in a first position.
Figure 3B:
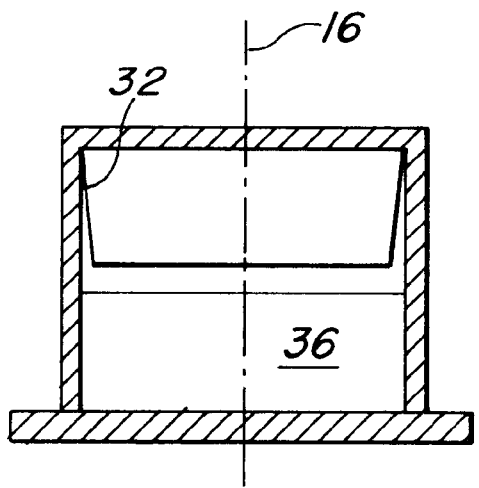
FIG. 3B is a cross-sectional view of the shunt valve of FIG. 1 along line 3—3 showing the anti-siphon mechanism in a second position.

To adjust the level of anti-siphon protection, the barrier 36 is movable between a first position or height (FIG. 3A) and a second position or height (FIG. 3B). The position of the barrier 36 corresponds to the threshold pressure that must be overcome to unseat the diaphragm 32 from the barrier. Once the diaphragm is dislodged from the barrier 36, CSF can flow from the first cavity 40 to the second cavity 42. Thus, the adjustable barrier 36 allows an operator to vary the volume of the first and second cavities 40 ,42 for achieving a desired anti-siphon protection level.

Figure 4:
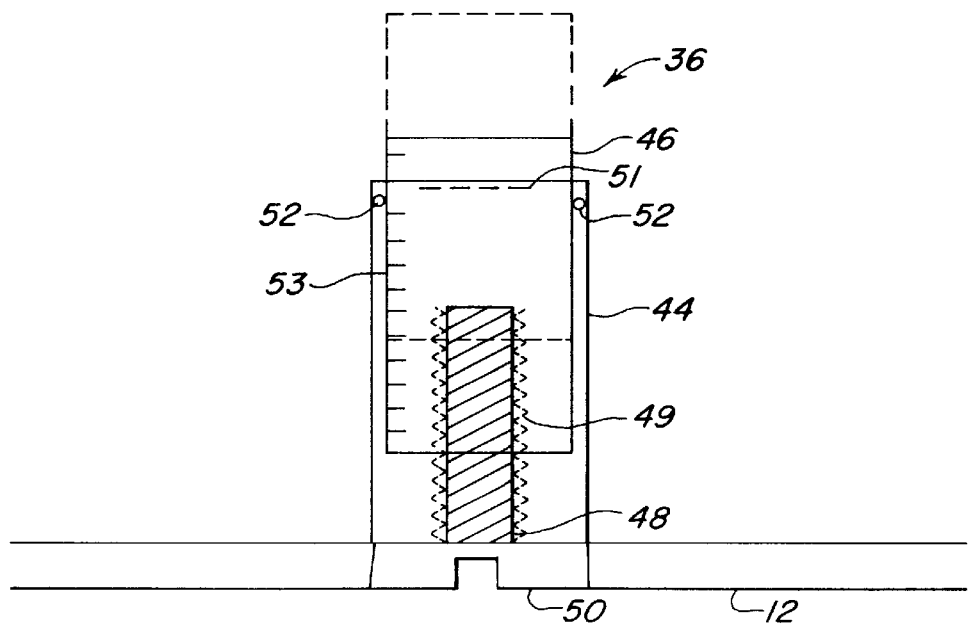
FIG. 4 is a cross-sectional view of the shunt valve of FIG. 1 along line 2—2 showing further details of the anti-siphon mechanism.

FIG. 4 shows an exemplary embodiment of the adjustable barrier 36 including an outer sleeve 44 and an extension member 46. The sleeve 44 is affixed about its perimeter to the interior surfaces of the housing so as to form a seal. The extension member 46 is movably captured in the sleeve 44.

The barrier 36 combines with the diaphragm 32 and the housing to prevent fluid communication between the two cavities 40 and 42 when the diaphragm 32 is seated on the barrier 36.

A seal 52 can be provided between the extension member 46 and the outer sleeve 44 to prevent fluid communication between the two cavities 40 and 42 as the height of the barrier is varied. In one embodiment, a screw mechanism is utilized to move the adjustable barrier 36. The screw mechanism can include a threaded rod 48 having a head 50 that extends through the housing 12 to allow the rod to be rotated. The configuration of the screw mechanism is such that the rod 48 maintains its position as the rod rotates. A bore in the solid extension member 46, in which the rod 48 is captured, has an internally threaded surface 49 which complements the threads on threaded rod 48. As the rod 48 is rotated the extension member 46 moves vertically to lower or raise the height of the barrier 36. The direction of rod 48 rotation determines in which direction the sleeve 44 moves.

The exposed head portion 50 of the rod is adapted to receive an adjustment tool (not shown), such as screw driver type tool. Adjustment of the barrier may be done percutaneously through a small incision in the scalp.

The adjustment mechanism 36 can optionally include a plurality of measurement marks 53 on the extension member 46 and a reference mark 52 on the sleeve 44 for determining the height or position of the barrier 36. The marks 53,55 can be radio opaque so that the height of the barrier 46 may be determined quickly and non-invasively by X-ray, CT, or MRI imaging.

After implantation, the implanted catheter 10 reduces or eliminates the siphon effect of the implanted shunt system. When the patient is in a generally recumbent position, CSF flows into the first cavity 40 causing the pressure exerted by the CSF against the diaphragm 32 to increase. When the fluid pressure within the first cavity 40 becomes greater than the pressure exerted by the diaphragm 32 against the barrier seat 38, a positive pressure gradient occurs and the diaphragm unseats from the seating surface 38 of the barrier. This allows CSF to flow from the first cavity 40 into the second cavity 42, through the outlet port 18, and ultimately to the discharge catheter. Thus, when the patient is generally horizontal, the shunt valve 10 does not offer significant resistance to the flow of CSF because the pressure differential between the first cavity 40 and the second cavity 42 is typically sufficient to overcome the reference pressure and any inherent bias exerted by the diaphragm 32 against the barrier 36.

When the patient's attitude changes, for example if the patient stands up, the shunt valve becomes substantially vertical such that the first cavity 40 is disposed above the second cavity 42. The fluid in the second cavity 42 then flows through the outlet port 20 until the pressure in the second cavity 42 becomes significantly lower than atmospheric pressure. The resultant negative pressure differential (a vacuum effect) tends to more firmly seat the diaphragm 32 against the barrier seating surface 38 to prevent fluid flow between the first and second cavities 40,42. Thus, the siphon effect of the shunt valve and tubing is substantially reduced or eliminated.

Figure 5:
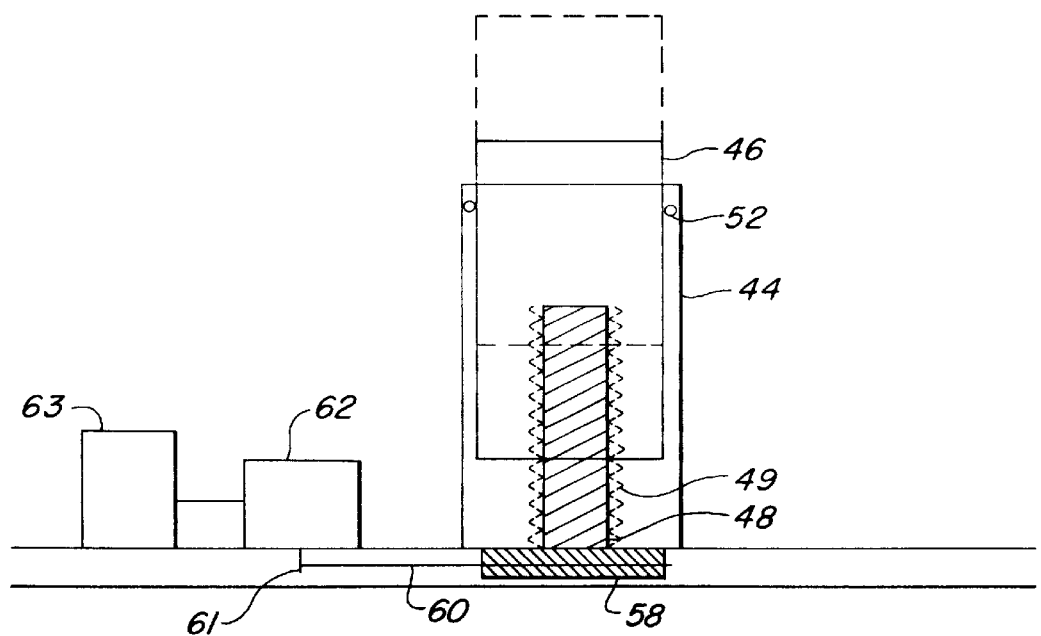
FIG. 5 is a diagrammatic representation of another embodiment of a shunt valve having an anti-siphon mechanism in accordance with the present invention.

FIG. 5 shows another embodiment of a shunt valve having an anti-siphon mechanism controlled by an electric motor 62 under the command of a controller 63 for rotating a shaft 61 with the rotational energy of the electric motor 62 being transferred by a belt 60 to a belt receiver 58. The belt receiver 58 is affixed to the threaded rod 48. The shaft 64 extends through the housing 12 and the belt 60 and belt receiver 58 are both disposed on the exterior of the housing 12. The belt receiver 58 can be sized relative to the shaft 64 so as to provide a suitable rotational velocity to the threaded rod 48. A optional spacer can be added to the shaft 64 in order to adjust the ratio of rotational velocities of the electric motor 62 and the threaded rod 48.

It is understood that the motor can be controlled by many different methods. For instance, a pressure switch located on the exterior of the housing and activated by pressing the appropriate location on the skin of the patient, a radio frequency signal, or an ultrasonic signal could be used to control the electric motor 62 as well. In addition, the belt 60 and belt receiver 58 may be replaced by a gear train of appropriate size and dimensions to provide the proper rotational velocity of the threaded rod 48.

Figure 6:
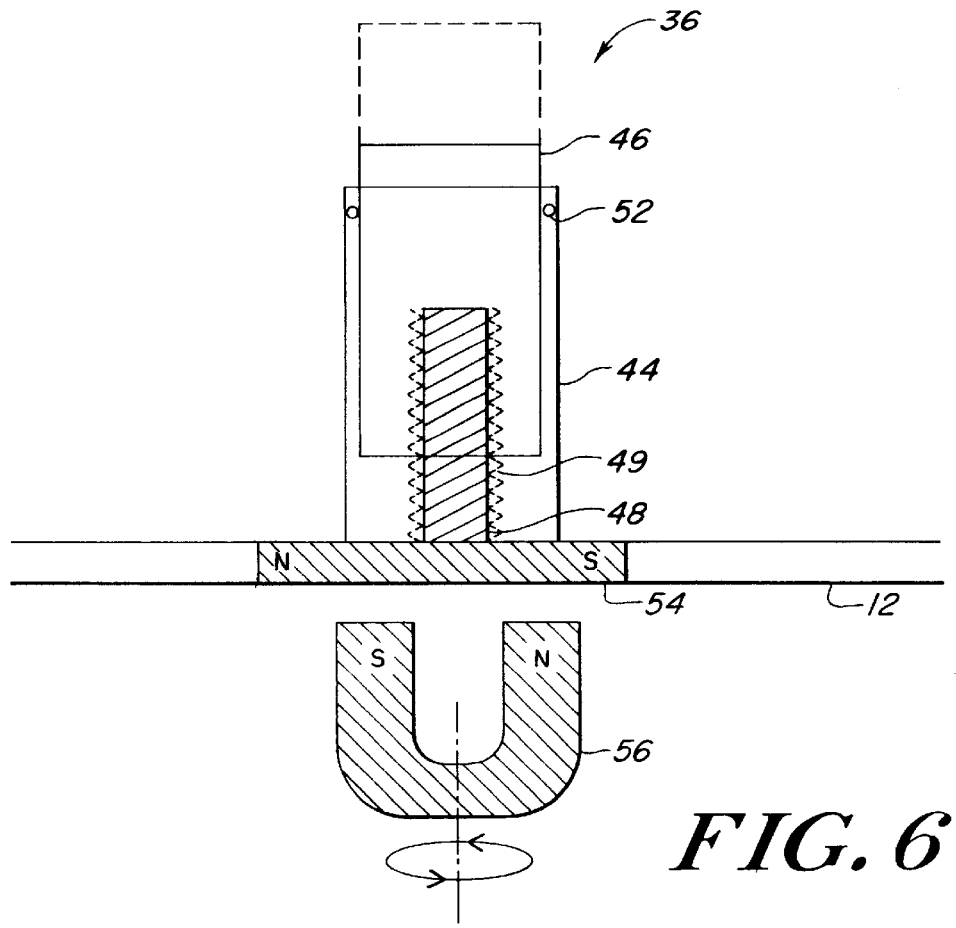
FIG. 6 is a diagrammatic representation of a further embodiment of a shunt valve having an anti-siphon mechanism in accordance with the present invention.

FIG. 6 shows a further embodiment of an anti-siphon mechanism, such as the mechanism shown in FIG. 4, controlled by a rotatable magnet. The head 54 of the rod includes at least one pair of magnets of opposite polarities. An externally applied magnetic field, which can be provided by remote device 56, is effective to cause rotation of the rod 48 for adjusting the height of the barrier 36. An exemplary external programming device for manipulating a rotating member having magnets contained therein is shown and described in U.S. Pat. No. 4,595,390 entitled "Magnetically-adjustable Cerebrospinal Fluid Shunt Valve," to Hakim et al. on Jun. 17, 1986 and incorporated herein by reference.

Figure 7:
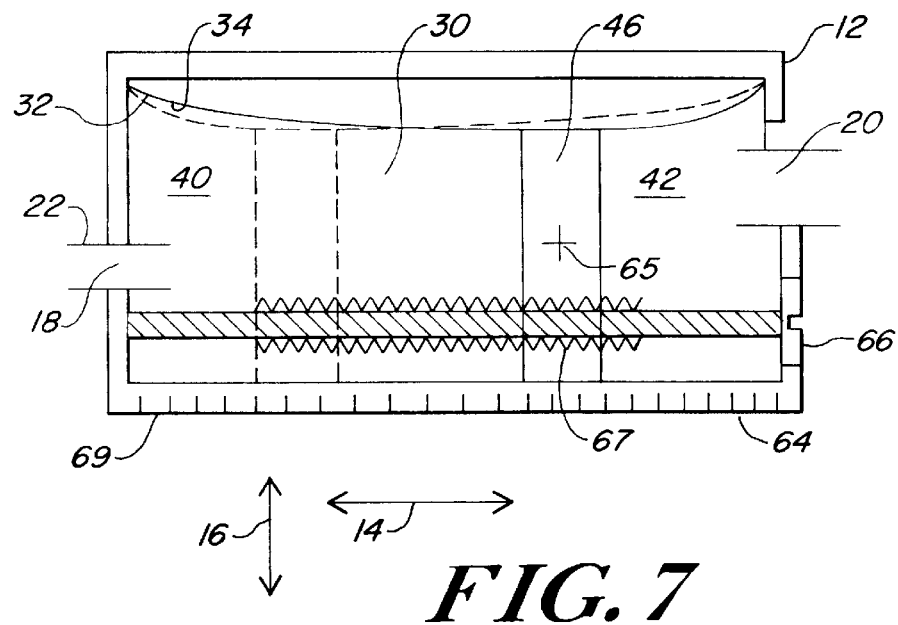
FIG. 7 is a longitudinal sectional view of another embodiment of an anti-siphon mechanism including an adjustable barrier that moves longitudinally.

FIG. 7 shows a further embodiment of an anti-siphon shunt valve 10 in which identical numbers refer to identical parts shown in FIG. 1. In this embodiment, the adjustable barrier 46 is adapted for movement along the longitudinal axis 14 of the housing 12. As the adjustable barrier 46 is moved along the longitudinal axis 14, the size of each of the first and second cavities 40, 42 is altered. The pressure differential required to overcome the bias of the diaphragm is proportional to the relative sizes of the first and second cavities 40 and 42. Thus, as the adjustable barrier 46 moves longitudinally, the volumetric ratio of the cavities 40, 42 changes concomitantly thereby modifying the level of anti-siphon protection.

In an exemplary embodiment, the anti-siphon mechanism comprises a barrier 46 having a hole and a threaded internal lumen 67 to receive a complementary set of threads on rod 64. The barrier 46 and rod 64 are connected in a worm gear relationship whereby rotation of the rod 64, via the head 66, effects linear movement of the barrier 46. The threaded rod 66 has a head portion 68 on the exterior of the housing 12 and the threaded rod 66 extends through a an opening in the wall of housing 12 designed to secure the threaded rod 64 so as to prevent any longitudinal movement thereof. The threaded rod 64 passes through the internal chamber 30 along the longitudinal axis 14 and is seated in a recess the opposite wall.

The barrier 46 is moveable along the interior surfaces of the internal chamber 30 not covered by the diaphragm 32 so as to seal off the first and second cavities 40,42 and thereby prevent fluid flow through the device. As the threaded rod 64 is rotated, the barrier 46 will be moved along the longitudinal axis 14 of the internal chamber. The head portion 66 is adapted to receive an adjustment tool (not shown) for rotating the threaded rod 64.

The barrier 46 can include a reference mark 65, which can be radio opaque, in the center of the barrier 46. The wall of the housing 12 can include measurement marks 69 that allow the position of the barrier 46 to be determined using an external viewing system, such as an X-ray machine.

Figure 8:
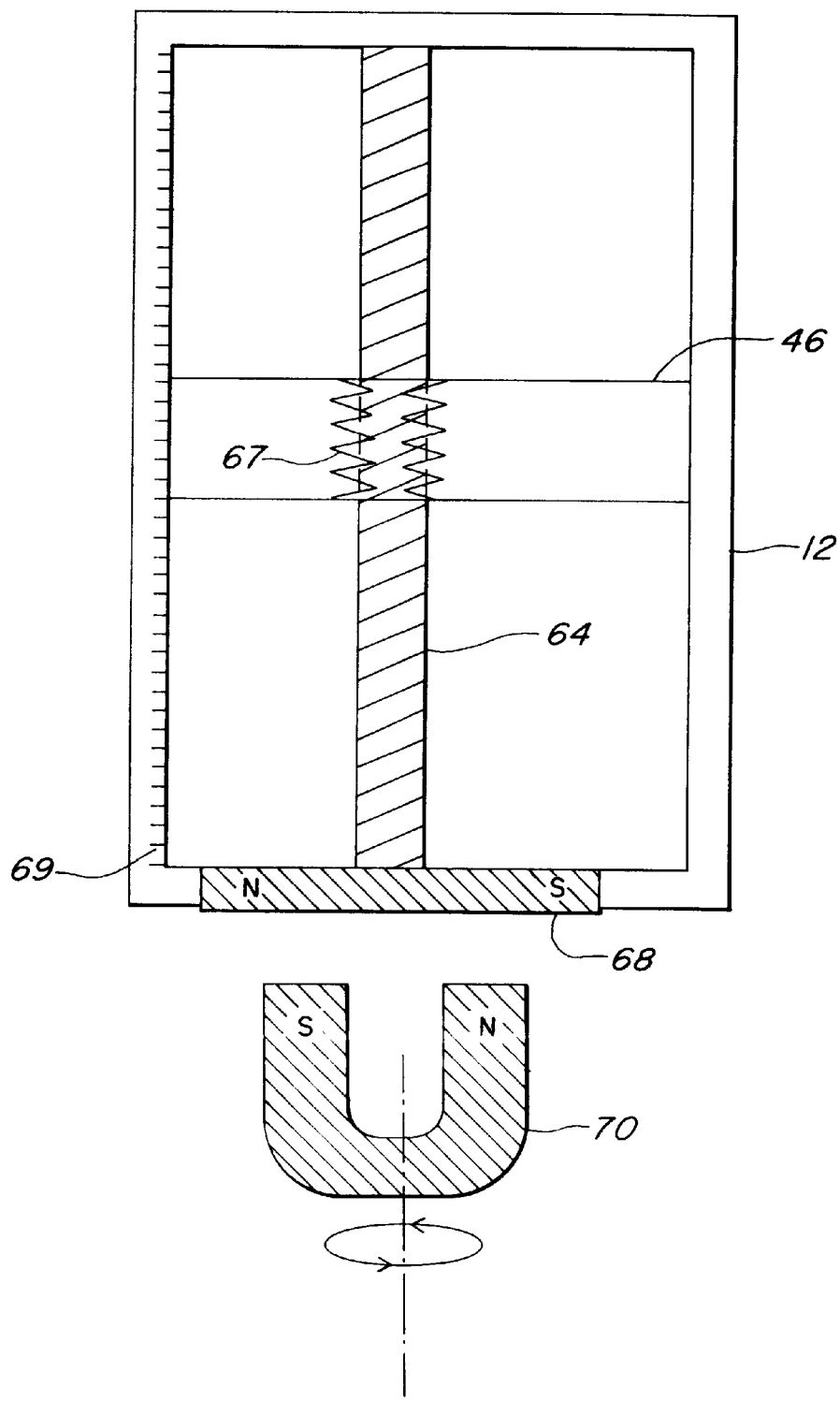
FIG. 8 is diagrammatic representation of the shunt valve of FIG. 7 that is adjustable using an external programming device.

In an alternative embodiment shown in FIG. 8, the barrier may be adjusted by a remote control mechanism, such as external device including a rotating magnet 70 for applying a magnetic field to rotate the rod.

Figure 9:
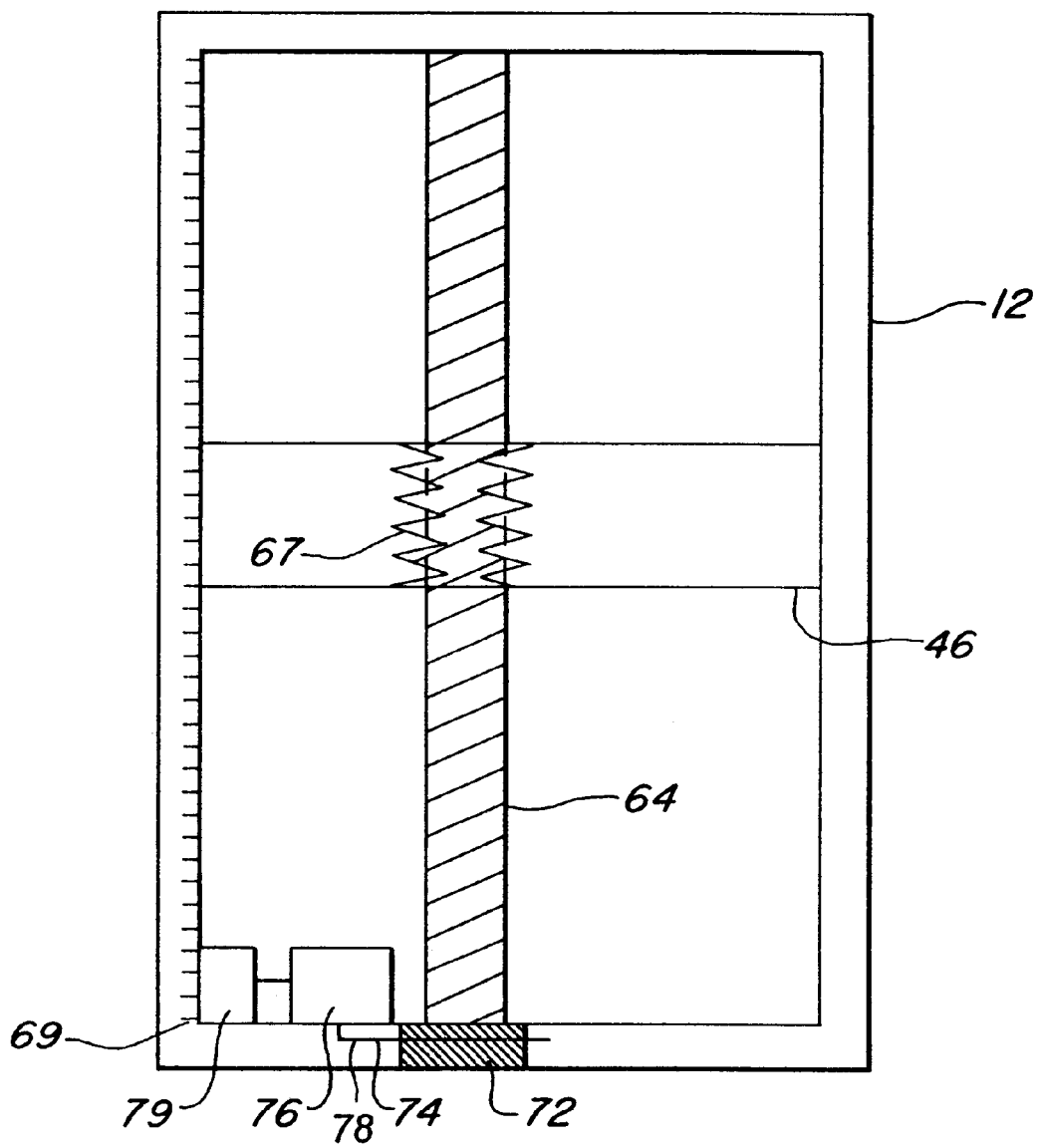
FIG. 9 is diagrammatic representation of the shunt valve of FIG. 7 that is adjustable using an electric motor.

FIG. 9 shows another embodiment of an anti-siphon shunt valve 10 in which a controller 79 controls an electric motor 76 that rotates a shaft 78 and the rotational energy of the electric motor 76 is transferred by a belt 74 to a belt receiver 72. The belt receiver 72 is affixed to the threaded rod 64. The shaft 78 extends through the housing 12 and the belt 74 and belt receiver 72 are both disposed on the exterior of the housing 12. The belt receiver 72 can be sized relative to the shaft 78 to provide a suitable rotational velocity to the threaded rod 64.

Figure 10:
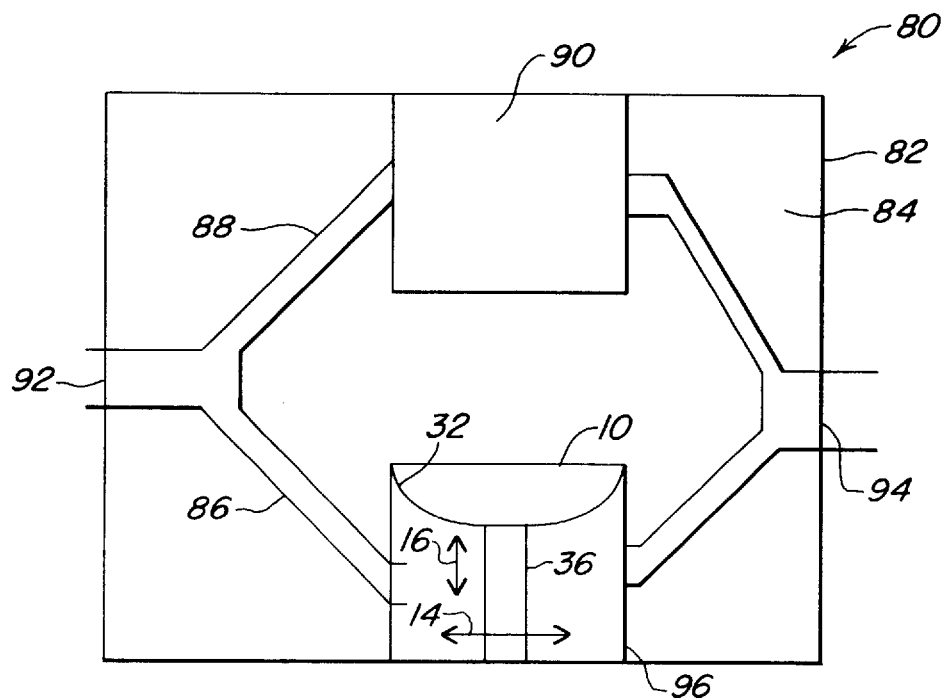
FIG. 10 shows another embodiment of a shunt valve having an anti-siphon mechanism utilizing parallel fluid paths.

FIG. 10 is another embodiment of an anti-siphon shunt valve 80 in accordance with the present invention. The shunt valve includes a housing 82 having a first inner chamber 84 and a second chamber 96 which houses an anti-siphon valve 10 having a diaphragm 32 and an adjustable barrier 36 which may move in either the longitudinal axis 14 or vertical axis 16. The first inner chamber has an inlet 92 and an outlet 94, a first fluid pathway 86 and a second fluid pathway 88 that provide parallel and alternative pathways through the chamber 84. An anti-siphon device 10, which can be provided as one of the devices of FIGS. 2–9, is inserted in the first fluid pathway 86 between the inlet 92 and the outlet 94, and a high resistance valve 90 is inserted in series between the inlet 92 and the outlet 94 in the second fluid pathway 88.

Cerebral spinal fluid flows into the inlet 92 and into one of the two fluid pathways 86 or 88. Fluid flowing into the high resistance valve 90 via fluid pathway 88 will meet a high flow resistance and will backup the fluid pathway 88 forcing fluid to flow through the lower resistance fluid pathway 86 into the anti-siphon valve 10 in chamber 96. As discussed above, the anti-siphon valve exhibits a relatively low fluid flow resistance when the patient is recumbent. The cerebral spinal fluid will flow with little or no resistance from the inlet 92 through the first fluid path 86 through the anti-siphon valve 10 and to the outlet 94 under normal circumstances. When the patient's orientation changes, i.e., when the patient stands up, the anti-siphon valve 10 will exhibit a high fluid flow resistance that is greater than the fluid flow resistance of the high resistance valve 90. In this way, should the cerebral spinal pressure increase to dangerous levels while the patient is standing up, the high resistance valve 90 will open and allow fluid to flow from the inlet 92 through the second pathway 88 to the outlet 94, reducing the pressure buildup within the cerebral ventricles even in the presence of the patient's vertical orientation.

The high resistance valve 90 may be any fluid valve which can be preset to a particular value of opening pressure. The high resistance valve 90 may be a spherical ball check valve, a movable closure means valve such as a diaphragm, or a valve element that includes a pair of slits therein that plastically deform at a calculated pressure differential, thereby opening to allow fluid flow.

Figure 11:
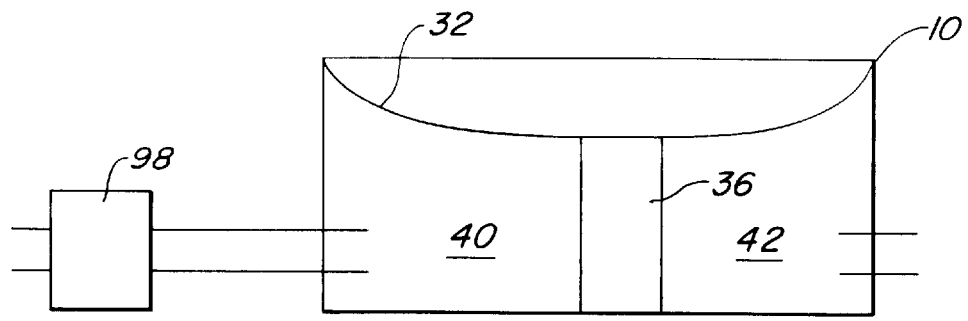
FIG. 11 shows another embodiment of the present invention with a pressure telesensor in series with an anti-siphon device.

FIG. 11 shows an anti-siphon shunt valve including a device 98 which monitors pressure waves in the system and transmits this pressure data to a receiving unit (not shown) external to the patient. The device 98 can be provided as a pressure telesensor, such as a telesensor device made by the Radionics Company of Burlington, Massachusetts. The pressure telesensor 98 provides pressure data to a remote receiving unit (not shown) which is used by the physician to interpret the pressure information to adjust the variable anti-siphon device for optimizing the level of anti-siphon protection in treating the patient's condition.

Figure 12:
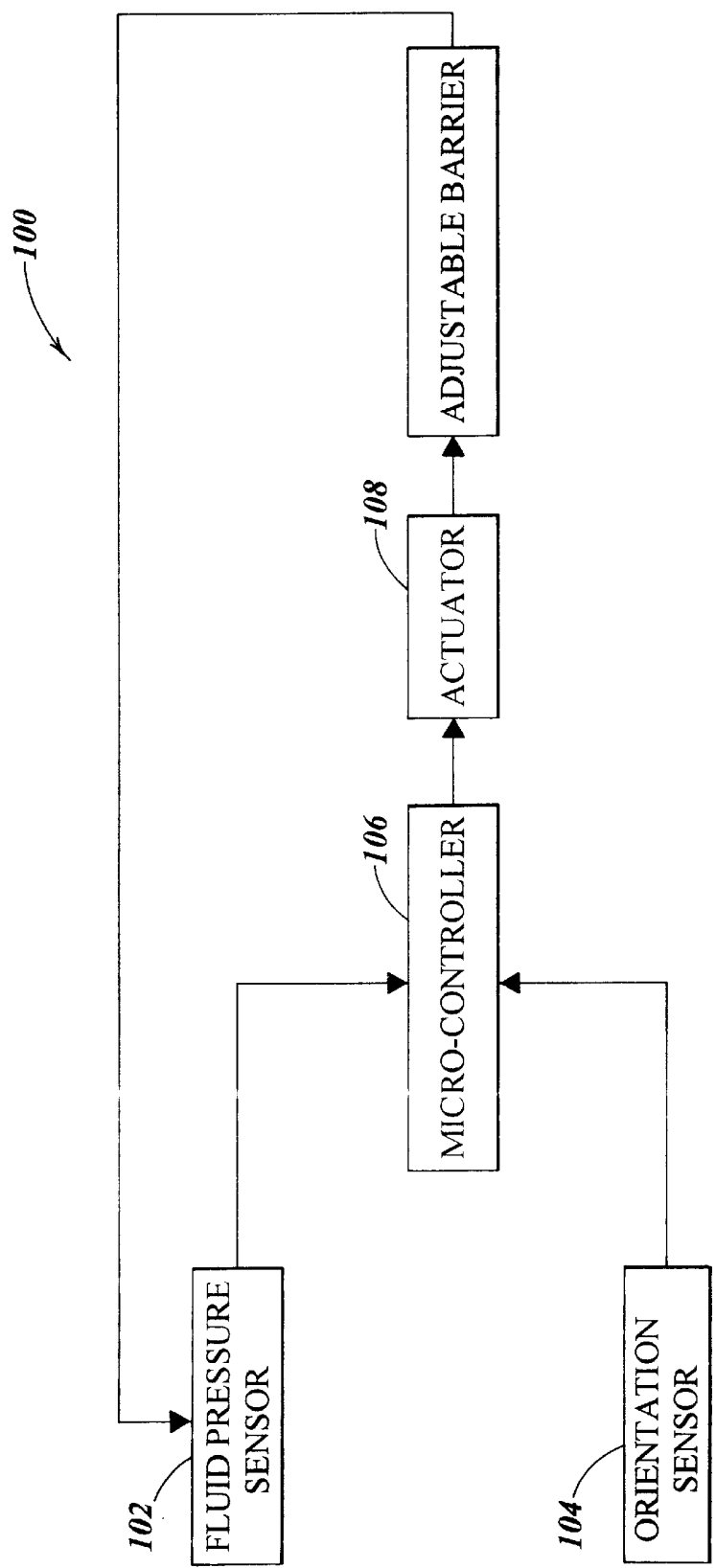
FIG. 12 is a block diagram of an anti-siphon shunt valve having a feedback control system in accordance with the present invention.

FIG. 12 shows a closed loop feedback control system for automatically adjusting the barrier in the anti-siphon device, such as the devices shown in FIGS. 2–11. The feedback control system 100 includes a fluid sensor 102, which measures fluid pressure, placed in series with the inlet of the anti-siphon device 10 in order to measure the fluid parameters, and provides this data to the controller 106. The controller has an additional input from an orientation sensor 104, which provides data on the orientation of the housing of the anti-siphon device in order to determine if the patient is recumbent or vertical. The controller 106 sends control signals to an actuator 108 which then adjusts the adjustable barrier in the anti-siphon device in order to provide optimal treatment conditions for patient.

The controller 106 can be implemented by a programmable microprocessor which is implanted within the housing of the anti-siphon device to perform all measurement and control functions in vivo, or it can be external to the patient and utilized to remotely set the operating parameters for the anti-siphon device. The actuator 108 can control the adjustable barrier via an electromechanical or magnetomechanical means. The choice of the operational parameters and operating points are well within the ordinary skill of one skilled in the art.

It is understood that the geometry, dimensions, and materials can vary depending upon the requirements of particular applications and the anatomy of the patient. The housing can be constructed from suitable non-toxic and bioimplantable materials, such as medical grade silicones and plastics. In one embodiment, the housing is constructed of an injection molded plastic. Although the housing is primarily shown and described as having a rectangular shape, it is understood that other geometries are possible such as cylindrical and polygonal structures.

What is claimed is:

1. An implantable catheter device having an adjustable level of anti-siphon protection, comprising:
    a housing having a longitudinal axis and inlet and outlet passages, the housing having a chamber formed therein;
    a deformable diaphragm coupled to the housing so as to form a portion of the chamber; and
    an adjustable barrier disposed within the chamber so as to form first and second cavities, the barrier being adapted for forming a seal with the diaphragm to provide anti-siphon protection by preventing fluid flow between the first and second cavities when the pressure in the second cavity drops below a threshold, wherein the threshold pressure value is adjusted by movement of the barrier.

2. A device as in claim 1 wherein the adjustable barrier has an adjustable height.

3. A device as in claim 2 wherein the adjustable barrier comprises a screw mechanism having a threaded rod, the adjustable barrier having an internally threaded surface to receive a mating set of threads on the threaded rod for adjusting the height of the adjustable barrier.

4. A device as in claim 3 wherein one end of the threaded rod is exposed to the exterior of the housing for external adjustment of the rod and thereby adjusting the height of the adjustable barrier.

5. A device as in claim 2 wherein the adjustable barrier further comprises a magnetic element mounted to the threaded rod for inducing rotation of the threaded rod in response to a magnetic field.

6. A device as in claim 2 further comprising an electric motor coupled for rotating the threaded rod.

7. A device as in claim 2 further comprising a first set of radio opaque markings on the adjustable barrier for determining the height of the adjustable barrier using an external imaging system.

8. A device as in claim 1 wherein the adjustable barrier is adjustable in position along the longitudinal axis of the housing.

9. A device as in claim 8 wherein the adjustable barrier comprises a threaded member within the housing, the adjustable barrier having a hole, the hole having a threaded internal bore for receiving the threaded member in a worm gear relationship, whereby rotation of the threaded member effects linear movement of the adjustable barrier.

10. A device as in claim 9 wherein the threaded member has one end exposed to the exterior of the housing for externally rotating the threaded member and moving the adjustable barrier.

11. A device as in claim 8 wherein the adjustable barrier further comprises a magnetic element mounted to the threaded rod for providing rotation to the threaded rod in response to an applied magnetic field.

12. A device as in claim 9 wherein the adjustable barrier further comprises an electric motor coupled to the threaded member for rotating the threaded member.

13. A device as in claim 8 furher comprising a first set of radio opaque markings on the adjustable barrier and a second set of radio opaque markings on the housing for determining the position of the adjustable barrier using an external imaging system.

14. A device as in claim 1, wherein a first fluid pathway extends from the inlet passage, through the first and second cavities, and to the outlet passage and further comprising:
    a second fluid pathway having a high resistance valve in series therein, the high resistance valve having a flow resistance greater than that of the barrier and the diaphragm in the first fluid pathway.

15. An implantable catheter device having an adjustable level of anti-siphon protection, comprising:
    a housing having a longitudinal axis and inlet and outlet passages, the housing having a chamber formed therein;
    a deformable diaphragm coupled to the housing so as to form a portion of the chamber; and
    an adjustable barrier disposed within the chamber so as to form first and second cavities, wherein the barrier, when the device is generally horizontal, is adapted for forming a seal with the diaphragm to prevent fluid flow between the first and second cavities when the pressure in the second cavity drops below a threshold value, and wherein the barrier, when the device is generally vertical, is adapted for forming a seal with the diaphragm to prevent the flow of fluid from the first cavity into the second cavity as fluid exits the second cavity to create a negative pressure differential that is effective to combat a siphon effect of the device.

16. An anti-siphon device comprising:
    a housing with an inlet and outlet fluid passage,
    a first fluid pathway extending from the inlet passage to the outlet passage;
    an anti-sophon valve disposed in the first fluid pathway, the valve having a deformable diaphragm and an adjustable barrier disposed within the valve for forming a first and second cavity, the adjustable barrier being adapted to contact the deformable diaphragm to preclude fluid passage through the first and second cavities of the anti-siphon valve when the pressure in the second cavity drops below a threshold pressure gradient, the adjustable barrier being moveable to adjust the threshold pressure differential; and a second fluid path, parallel to and alternate to the first fluid path, the second fluid path having a high flow resistance valve in series therein, the high fluid flow resistance value having a fluid flow resistance greater than the threshold pressure gradient.

17. An anti-siphon device as in claim 16 wherein the adjustable barrier comprises an adjustable screw set within the adjustable barrier for adjusting the height of the adjustable barrier.

18. An anti-siphon device as in claim 17 wherein one end of the adjustable screw is exposed to the exterior of the housing to provide for external adjustment to the adjustment screw and thereby adjusting the height of the adjustable barrier.

19. An anti-siphon device as in claim 17 wherein the adjustable barrier further comprises a magnetic element mounted to the adjustment screw for providing rotation of the adjustment screw in response to a rotating magnetic field.

20. An anti-siphon device as in claim 17 wherein the adjustable barrier further comprises an electric motor coupled to the adjustment screw to rotate the adjustment screw in response to an electrical signal.

21. An anti-siphon device as in claim 16 wherein the anti-siphon device further comprises a first set of radio opaque markings on the adjustable barrier for determining the height of the adjustable barrier by x-rays.

22. An anti-siphon device as in claim 16 wherein the adjustable barrier is adjustable in position along the longitudinal axis of the housing.

23. An anti-siphon device as in claim 22 wherein the adjustable barrier comprises a threaded member within the housing, the adjustable barrier having a hole to threadably receive the threaded member, whereby when the threaded member is rotated the adjustable barrier is moved along the threaded member.

24. An anti-siphon device as in claim 23 wherein the threaded member has one end exposed to the exterior of the housing for externally rotating the threaded member and moving the adjustable barrier.

25. An anti-siphon device as in claim 23 wherein the adjustable barrier further comprises a magnetic element mounted to the threaded member for providing rotation to the threaded rod in response to a rotated magnetic field.

26. An anti-siphon device as in claim 22 wherein the adjustable barrier further comprises an electric motor coupled to an adjustment screw to rotate the adjustment screw in response to an electrical signal.

27. An anti-siphon device as in claim 22 wherein the anti-siphon device further comprises a first set of radio opaque markings on the adjustable barrier and a second set of radio opaque markings on the housing for determining the position of the adjustable barrier by x-rays.

28. An anti-siphon device comprising:

a housing having an chamber, and an inlet and outlet for fluid passage through the chamber, an adjustable barrier disposed within the so as to form first and second cavities, the barrier being adapted to contact a diaphragm to preclude fluid passage between the first and second cavities when the pressure is the second cavity drops below a selected pressure gradient, the barrier being moveable to adjust the pressure gradient, and a fluid pressure telesensor in series with the inlet for measuring waves of the fluid entering the inlet and transmitting the pressure valves to a processor that controls the barrier height.

29. An anti-siphon device comprising:

a housing having a chamber, and an inlet and outlet for fluid passage through the chamber, an adjustable barrier disposed within the chamber so as to form first and second cavities, the barrier being adapted to compact a diaphragm to preclude fluid passage between the first and second cavities when the pressure in the second cavity drops below a defined pressure gradient, the barrier being moveable to adjust the pressure gradient, a fluid pressure sensor in series with the inlet, a orientation sensor mounted on the housing, for providing data on the orientation of the housing, and a controller, having a first input of fluid pressure data from the pressure sensor, a second input of orientation data from the orientation sensor, and an output controlling the position of the adjustable barrier for optimally controlling the fluid pressure at a given orientation.

30. A method of anti-siphon protection in a valve comprising, installing in a patient a valve having an adjustable level of anti-siphon protection, the valve comprising:

a housing having a longitudinal axis and inlet and outlet passages, the housing having a chamber formed therein;

a deformable diaphragm coupled to the housing so as to form a portion of the chamber; and an adjustable barrier disposed within the chamber so as to form first and second cavities, the barrier being adapted for forming a seal with the diaphragm to provide anti-siphon protection by preventing fluid flow between the first and second cavities when the pressure in the second cavity drops below a threshold value, wherein the threshold pressure value is adjusted by movement of the barrier; and moving the adjustable barrier within the valve to adjust an opening pressure of the valve to a selected pressure.

31. The method of claim 30 wherein the movement of the adjustable barrier is vertical.

32. The method of claim 30 wherein the movement of the adjustable barrier is longitudinal.

33. The method of claim 30 further comprising applying an external magnetic field for effecting movement of the adjustable barrier.

34. The method of claim 30 further comprising applying a control signal to an electric motor for effecting movement of the adjustable barrier.

35. The method of claim 30 further comprising measuring fluid pressure within the valve.

36. The method of claim 30 further comprising the steps of:

measuring the fluid pressure within the valve, determining the orientation of the valve, calculating an opening pressure for the valve, and moving the adjustable barrier to achieve the calculated opening pressure.

* * * * *